United States Patent
Goldberg et al.

(10) Patent No.: US 8,199,328 B2
(45) Date of Patent: Jun. 12, 2012

(54) POLARIMETER EMPLOYING A FIZEAU INTERFEROMETER

(75) Inventors: Doron Goldberg, Metula (IL); Zeev Weissman, Ness Ziona (IL)

(73) Assignee: Mellitor Ltd., Katzrin (IL)

(*) Notice: Subject to any disclaimer, the term of this patent is extended or adjusted under 35 U.S.C. 154(b) by 204 days.

(21) Appl. No.: 12/745,258

(22) PCT Filed: Nov. 26, 2008

(86) PCT No.: PCT/IL2008/001547
§ 371 (c)(1), (2), (4) Date: May 28, 2010

(87) PCT Pub. No.: WO2009/069127
PCT Pub. Date: Jun. 4, 2009

(65) Prior Publication Data
US 2010/0259759 A1  Oct. 14, 2010

Related U.S. Application Data

(60) Provisional application No. 60/990,782, filed on Nov. 28, 2007.

(51) Int. Cl.
*G01B 9/02* (2006.01)
(52) U.S. Cl. .................................... 356/491
(58) Field of Classification Search .......... 356/366, 356/367, 491
See application file for complete search history.

(56) References Cited

U.S. PATENT DOCUMENTS

| | | | | |
|---|---|---|---|---|
| 4,643,575 A | * | 2/1987 | Hazeltine et al. | 356/487 |
| 5,644,398 A | * | 7/1997 | Yoshida | 356/484 |
| 5,896,198 A | | 4/1999 | Chou et al. | |
| 6,128,080 A | * | 10/2000 | Janik et al. | 356/491 |
| 6,188,477 B1 | | 2/2001 | Pu et al. | |
| 6,327,037 B1 | | 12/2001 | Chou | |
| 2008/0062428 A1 | * | 3/2008 | Millerd et al. | 356/492 |

FOREIGN PATENT DOCUMENTS

| | | |
|---|---|---|
| EP | 1387161 A | 2/2004 |
| GB | 2164172 A | 3/1986 |
| JP | 03195907 A | 8/1991 |
| WO | 2008018079 A2 | 2/2008 |

OTHER PUBLICATIONS

King et al; "Optical heterodyne polarimeter for measuring the chiral parameter and the circular refraction indices of optical activity" Optics Letters vol. 18, No. 22 (1993).
Jacobs., "Optical heterodyne (coherent) detection" American Journal of Physics vol. 56, Issue 3, pp. 235 (1988).

* cited by examiner

*Primary Examiner* — Tarifur Chowdhury
*Assistant Examiner* — Jonathon Cook
(74) *Attorney, Agent, or Firm* — Browdy and Neimark, PLLC

(57) ABSTRACT

A polarimeter based on a modified Fizeau interferometer and a method for measuring the optical rotation of a polarized light beam by an optically active substance using the polarimeter, are provided.

17 Claims, 3 Drawing Sheets

POLARIMETER EMPLOYING A FIZEAU INTERFEROMETER

FIELD OF THE INVENTION

The present invention relates to a method and a device for the measurement of the rotation of linearly polarized light, which are suitable for applications such as the monitoring of the concentration of optically active substances in a solution. The detection device is based on a modified Fizeau interferometer and employs coherent detection to measure the optical rotation, with high sensitivity and resolution, while enabling the subtraction of background signals without the need to measure reference samples.

BACKGROUND OF THE INVENTION

The accurate measurement of the concentration of chiral molecules in a solution by a polarimeter is required in applications such as the synthesis of organic molecules, where the outcome of a reaction is a racemic mixture of both enantiomers, which have identical physicochemical characteristics except for the rotation of linearly polarized light. Enantiomers also interact differently with biological enzymes. Therefore, the ability to distinguish between the two enantiomers is especially crucial in the pharmaceutical industry, where in many cases only one enantiomer has the desired activity while the other can be highly toxic, although both are physically identical.

A more sensitive and accurate polarimeter may mean lower concentrations of precious reagents, faster development processes, and purer, safer products.

Polarimeters based on coherent detection (Jacobs, S. F., (1988), Optical heterodyne (coherent) detection, *Am. J. Phys.*, 56 (3): 235-245, and King, H. J., Chou, C., and Lu, S. T., Optical heterodyne polarimeter for measuring the chiral parameter and the circular refraction indices of optical activity, *Opt. Lett.*, 1993, 18: 1970-1972), have the advantage of being sensitive and accurate without any moving mechanical parts, which are required by ordinary polarimeters in order to rotate polarizers or move quartz plates. They also do not rely on bulky optical components, like Faraday rotators, which can be found in modern advanced polarimeters.

U.S. Pat. Nos. 5,896,198 and 6,327,037 disclose a heterodyne polarimeter employing a two-frequency laser source and a common path interferometer. However, this polarimeter cannot distinguish between a heterodyne signal resulting from increased optical activity in the solution or one resulting from increased polarization noise (i.e. anything other than optical activity allowing more light to reach the detector through the analyzer), which adds to the detected coherent signal. Such sources can be, for example, the finite extinction ratio of the polarizers, depolarization of the linearly polarized laser beam by scattering, temperature-dependent birefringence in optical elements and the practical imperfection of Zeeman lasers. These limitations can become important especially when reference (blank) samples cannot be measured. U.S. Pat. No. 6,188,477 discloses a polarimeter based on a self-homodyne scheme. Here too no distinction can be made between the optical activity dependent signal and signals generated by increased depolarization or phase noise in the optical system. This polarimeter also is likely to be sensitive to mechanical phase noise in the optical setup responsible for the phase modulation.

Recently, the inventors disclosed a polarimeter for quantitative measurement of the concentration of optically active substances in a solution by incorporating a Mach-Zehnder interferometer into a polarimeter (WO 2008/018079).

SUMMARY OF THE INVENTION

It is an object of the present invention to improve the accuracy of current polarimeters by using a coherent detection (heterodyne or homodyne) scheme based on a simple Fizeau-type interferometer.

According to a first aspect, the present invention relates to a method for measuring the optical rotation of a polarized light beam by an optically active substance, using a polarimeter based on a modified Fizeau interferometer, comprising the steps of:

a) generating by a laser a first coherent light beam of a first frequency;
b) linearly polarizing said first light beam by passing it through a polarizer so that its electric field vector becomes parallel to the main plane of the polarimeter, defined by the polarizer's transmission axis and the beam's direction;
c) directing said first linearly polarized light beam through a modified Fizeau interferometer, whereby:
   (i) said first linearly polarized light beam of a) is split, so that one part of it is reflected at an angle with respect to the original direction, and the other part is transmitted in the original direction;
   (ii) said transmitted first linearly polarized light beam is passed through a sample comprising an optically active substance and its electric field vector is rotated by said optically active substance;
   (iii) said transmitted first linearly polarized light beam is then partially reflected and partially transmitted, so that second and third linearly polarized light beams are generated, and said second linearly polarized light beam, which is reflected, is a reference beam, and said third linearly polarized light beam, which is transmitted, is a measurement beam;
   (iv) said linearly polarized reference beam returns along the path of said first light beam through the sample and its electric field vector is rotated by said optically active substance in the sample, so that said linearly polarized reference beam accumulates no net optical rotation with respect to said first linearly polarized light beam;
   (v) the electric field vector of said measurement beam is rotated by mirroring it around an axis set at 45 degrees with respect to the polarimeter's main plane;
   (vi) the optical frequency of said measurement beam, with rotated electric field vector, is shifted by an amount ranging from several hundred Hertz to several kilohertz, so that said measurement beam, with rotated electric field vector, now has a second frequency different from said first frequency;
   (vii) said measurement beam, with rotated electric field vector and second frequency, is completely reflected, so that it returns along its original path through said sample of optically active substance;
   (viii) the electric field vector of said linearly polarized measurement beam is rotated on its way back through said sample by said optically active substance, so that the optical rotation of said linearly polarized measurement beam, imparted by said optically active substance, is doubled with respect to said first linearly polarized light beam;

(ix) said linearly polarized reference and measurement light beams transmitted by said sample are combined and interfere to generate a fourth light beam;

d) splitting said fourth light beam into fifth and sixth linearly polarized orthogonal light beams;

e) directing said fifth linearly polarized light beam, whose electric field vector is perpendicular to the polarimeter's main plane, to a reference photodetector and generating a reference signal;

f) directing said sixth linearly polarized light beam, whose electric field vector is parallel to the polarimeter's main plane, to a measurement photodetector and generating a coherently detected measurement signal; and g) storing and processing said reference and measurement signals and generating comparison signals using said reference and measurement signals, said comparison signals indicating the polarization rotation angle imparted to said linearly polarized measurement light beam by said optically active substance.

In another aspect, the present invention relates to a polarimeter for measuring the optical rotation of a linearly polarized light beam by an optically active substance, comprising:

a) a laser source for generating a first coherent light beam of a first frequency;

b) a polarizer for linearly polarizing said first light beam, whose transmission axis, together with the beam's direction, defines the main plane of the polarimeter;

c) a modified Fizeau interferometer comprising:

(i) a beam splitter for splitting said first linearly polarized light beam, so that one part of it is reflected at an angle with respect to the original direction, and the other part is transmitted in the original direction;

(ii) means for holding a sample comprising an optically active substance on the path of said transmitted part of said first linearly polarized light beam;

(iii) a partially reflecting mirror placed after the means for holding a sample comprising an optically active substance for generating second and third linearly polarized light beams from said transmitted first linearly polarized light beam, said second linearly polarized light beam, which is reflected exactly in the reverse direction, is a reference beam, and said third linearly polarized light beam, which is transmitted in the original direction, is a measurement beam;

(iv) a quarter $\lambda$ wave-plate, whose fast axis is set at 45 degrees with respect to the polarimeter's main plane, for rotating the electric field vector of said linearly polarized measurement beam;

(v) a frequency shifter, for shifting the optical frequency of said measurement beam, with said rotated electric field vector, so that said linearly polarized measurement beam will have a second frequency different from said first frequency;

(vi) a fully reflecting mirror for reflecting said measurement beam, with said rotated electric field vector, and said second frequency exactly in the reverse direction, whereby said reflected measurement beam returns along its original path through said quarter waveplate, so that its electric field vector is rotated by mirroring it around an axis set at 45 degrees with respect to the polarimeter's main plane, and said measurement beam transmitted by said quarter $\lambda$ waveplate then passes through said sample, so that its electric field vector is rotated by said optically active substance, thereby doubling the optical rotation of the transmitted first linearly polarized light beam imparted by said optically active substance;

(vii) a beam combiner for combining and interfering said linearly polarized reference beam and measurement beam transmitted through said sample and generating a fourth light beam, wherein said beam combiner and said beam splitter of (i) are essentially the same optical element;

d) a polarizing beam splitter for splitting said fourth light beam into fifth and sixth linearly polarized orthogonal light beams;

e) a reference photodetector for receiving said fifth linearly polarized light beam and generating a reference signal;

f) a measurement photodetector for receiving said sixth linearly polarized light beam and generating a coherently detected measurement signal, proportional to the polarization rotation angle imparted to said linearly polarized measurement beam by said optically active substance; and g) electronic means for storing and processing said reference and measurement signals and for generating comparison signals using said reference and measurement signals, said comparison signals indicating the polarization rotation angle imparted to said linearly polarized measurement beam.

In preferred embodiments of the present invention, the method and the polarimeter are useful for quantitatively measuring the concentration of an optically active substance in a solution held in a measurement cell with transparent walls, but also the measuring of the optical activity of solid substances is encompassed by the present invention.

Without any optical activity in the measurement cell, and assuming ideal polarizer, wave-plate and polarizing beam splitter are employed, both the reference and measurement beams will be perfectly orthogonal and no heterodyne signal should be detected. An optically active substance in the measurement cell, on the other hand, will rotate the electric field vector of the frequency-shifted measurement beam, and a heterodyne signal at the shifted frequency will be detected at the measurement photodetector. Since the reference beam's electric field vector is not rotated by the optically active substance, it has, ideally, no component which can reach the reference detector and generate there a heterodyne signal.

Practically, a background heterodyne signal can be generated at both detectors even without an optically active substance in the measurement cell. Possible sources for this background signal could be the finite extinction ratio of the polarizers, depolarization by scattering, and temperature-induced birefringence. Since no heterodyne signal can be generated at the reference detector by optical activity, it can be used to assess the contribution of the background signal to the total amplitude of the heterodyne signal.

The Fizeau-based setup is prone to interference by multiple reflections between the partially reflecting mirror and the fully reflecting mirror. Such multiple reflections can generate additional, weak heterodyne signals at multiples of the expected frequency, which exponentially decay at higher frequencies. These unwanted heterodyne signals can be minimized either by using a suitable anti-reflection coating, or by placing the partially reflecting mirror outside the main optical axis of the modified Fizeau interferometer, perpendicularly to the main optical axis. In this case a second beam splitter is placed between the means for holding the optically active substance and the quarter $\lambda$ wave-plate. The second beam splitter is for splitting the first linearly polarized beam into measurement and reference linearly polarized beams, and the partially reflecting mirror is for reflecting the reference linearly polarized beam back to the second beam splitter. In a preferred embodiment, the partially reflecting mirror is replaced by a fully reflecting mirror and the second beam splitter is an asymmetric beam splitter.

The modified setup, with the additional beam splitter, causes loss of some laser power, but it enables the use of laser sources with short coherence length, since the paths of the reference and measurement beams can now be made nominally equal.

The Fizeau-based heterodyne polarimeter used in accordance with the present invention has several advantages: 1) the reference and measurement beams share a common path, making the polarimeter less susceptible to vibrations at the expense of laser power; 2) because only one laser source is used, laser phase noise and power fluctuations can be canceled; 3) the effect of low-frequency phase noise, generated by vibrations and thermal effects, can be reduced by using the heterodyne signal of the reference photodetector; 4) any heterodyne signal, which is detected at the expected frequency by the reference detector, must result from polarization noise generated by various sources along the optical path and, therefore, their contribution to the total amplitude of the heterodyne signal can be subtracted; 5) the measurement cell is traversed twice by the measurement beam enabling the doubling of optical rotation; and 6) the optical setup is simple and no bulky, power-consuming components like Faraday rotators are required. Moreover, once the ratio between the reference and measurement heterodyne signals, at zero optical activity in the measurement cell, is established and remains constant, there is no further need to measure reference (blank) samples.

It should be understood by those skilled in the art that the frequency-shifted beam can be the reference beam instead of the measurement beam and that several different means can be used to generate the coherently detected signal. For example, a shift in the frequency of the measurement beam can be achieved by mounting the fully reflecting mirror on a PZT-actuated translation stage with a long (several hundred micrometers) traveling range, driven by a low frequency ramp or triangle waveform. In another example, a thin PZT disk, coated by a reflecting layer, can be used to modulate the phase of the measurement beam at a frequency ranging from several hundred Hertz to several megahertz, with a sine waveform and amplitude smaller than $\pi/2$. Such a phase modulation will create a coherently detected signal of the homodyne type, whose amplitude becomes maximal when the phase difference between the measurement and reference beams is around $\pi/2$.

DESCRIPTION OF THE PREFERRED EMBODIMENTS

The invention will now be illustrated by detailed description of the following non-limiting embodiments of the polarimeter of the invention, with reference to the figures. In the following detailed description of the embodiments, reference is made to the accompanying drawings that form a part thereof, and in which are shown by way of illustration specific embodiments in which the invention may be practiced. It is understood that other embodiments may be utilized and structural changes may be made without departing from the scope of the present invention.

Figure 1:
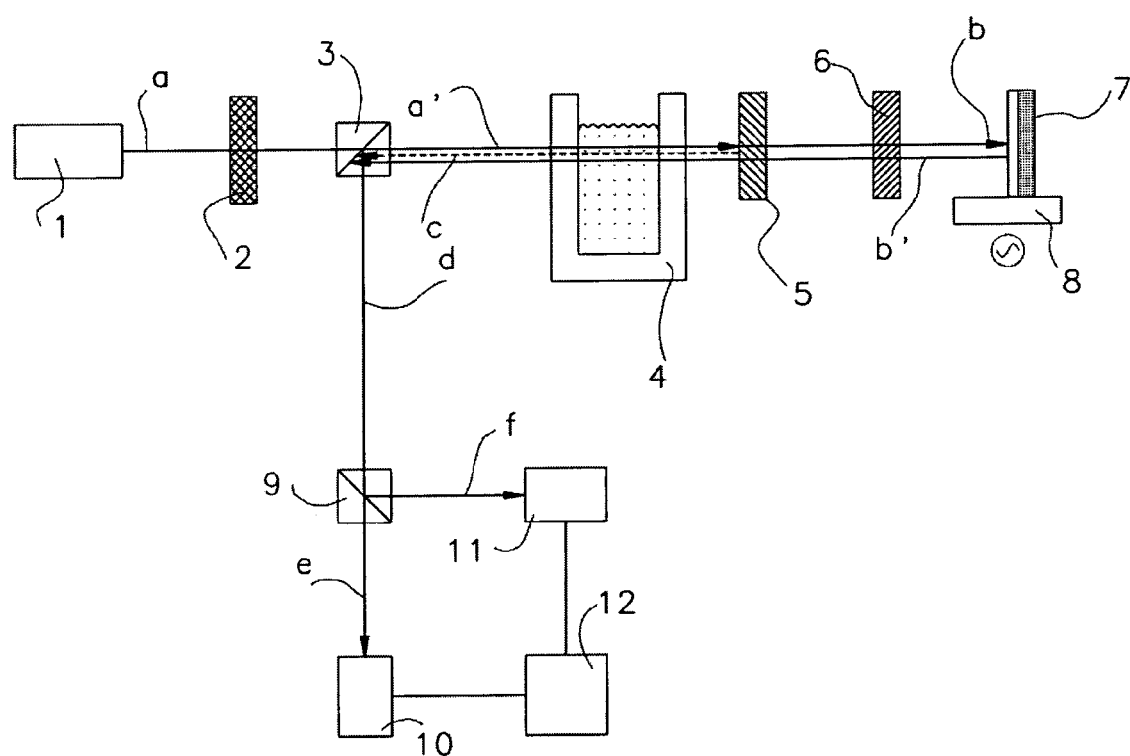
FIG. 1 is a block diagram of a polarimeter according to the first embodiment of the invention where light paths a, a', b, b', c and d of the Fizeau interferometer are formed, and a', b, b' and c share a common path along its main axis (they are only shown displaced for the sake of clarity). Light paths e and f belong to the detection setup. In the figure: 1. laser source; 2. polarizer; 3. 50:50 beam splitter/combiner; 4. measurement cell containing a solution of an optically active substance; 5. partially reflecting mirror; 6. quarter λ wave-plate (with its fast axis set at 45 degrees with respect to the polarimeter's main plane); 7. fully reflecting mirror mounted on a PZT-actuated translation stage; 8. PZT-actuated translation stage; 9. polarizing beam splitter; 10. reference detector; 11. measurement detector; 12. signal processing electronics.

FIG. 1 shows a scheme of a device for the quantitative determination of optically active substances in a solution, conforming to a first exemplary embodiment. The device includes a laser source that emits coherent light. The wavelength of the emitted light can typically range from 400 nanometers to 900 nanometers.

The laser source 1 generates a first coherent light beam (a). The first light beam (a) passes through a polarizer 2 and becomes linearly polarized. The first linearly polarized beam (a) passes through a 50:50 beam splitter/combiner 3 and is split into linearly polarized reflected and transmitted beams. The transmitted first linearly polarized beam (a') traverses the measurement cell 4, holding a solution of an optically active substance, whose concentration is to be determined, and its electric field vector is rotated by a certain amount by the optically active substance. When this linearly polarized beam (a') exits the measurement cell, it is split, asymmetrically, by a partially reflecting mirror 5 into a measurement (b) and reference (c) linearly polarized beams.

The linearly polarized reference beam (c), which typically acquires only 5-10% of the light intensity, is reflected exactly in the reverse direction, and passes again through the measurement cell 4. When the linearly polarized reference beam (c) traverses the measurement cell 4 in the reverse direction, its electric field vector is rotated by the optically active substance in the solution. However, this time the optical rotation cancels entirely the optical rotation accumulated during the passage of the first linearly polarized beam (a') in the forward direction and, therefore, the linearly polarized reference beam acquires no net optical rotation.

The linearly polarized measurement beam (b), which is transmitted by the partially reflecting mirror 5 in the original direction, passes through a quarter λ wave-plate 6, with a fast axis set at 45 degrees with respect to the polarimeter's main plane, and becomes temporarily circularly polarized. The circularly polarized measurement beam (b) is reflected in the reverse direction by a fully reflecting mirror 7, mounted on a piezo-actuated translation stage 8 having a long traveling range.

The piezo-actuated translation stage 8 is driven by a low frequency ramp or triangle waveform, moving the mirror several hundred micrometers in each cycle and shifting the optical frequency of the circularly polarized measurement beam (b) by the "Doppler effect". This frequency shift is typically in the range of several hundred Hertz to several kilohertz. The frequency-shifted and reflected circularly polarized measurement beam (b') passes again through the quarter λ wave-plate 6 and returns to be linearly polarized, with its electric field vector now mirrored about the fast axis of the quarter λ wave-plate 6. When no optical activity is present in the solution, this mirroring by the quarter λ wave-plate 6 rotates the electric field vector of the linearly polarized measurement beam (b') by exactly 90 degrees with respect to the polarimeter's main plane. When an optically active substance is present in the solution, the deviation from 90 degrees is proportional to its concentration.

The linearly polarized and frequency-shifted measurement beam (b') returns through the measurement cell and its electric field vector again is rotated by the optically active substance, so that its total optical rotation angle is doubled.

When both the linearly polarized reference (c) and measurement (b') beams reach the beam splitter/combiner 3 on their way back, they are combined and interfere with each other and 50 percents of the combined beam are directed to a polarizing beam splitter 9. The polarizing beam splitter 9 splits the combined beam into its two orthogonal components (e) and (f) and sends the horizontal component (f) to the reference detector 10 and the vertical components (e) to the measurement detector 11.

The vertical component (e), reaching the measurement detector 11, generates a coherently detected measurement signal of the heterodyne type, with a frequency which is determined by the velocity of the fully reflecting mirror 7. The amplitude of the coherently detected measurement signal represents the concentration of the optically active substance in the solution held in the measurement cell 4, as well as the amount of polarization noise along the optical path.

The dependence of the total measurement photocurrent ($I_m$), generated at the measurement detector 11, on the laser radiation and optical rotation angle-dependent and background heterodyne signals, is given by equation (1):

$$I_m \propto \sin 2\theta \cdot E_r E_m \cos(\Delta\omega t) + aE_r E_m \cos(\Delta\omega t) + DC \quad (1)$$

where θ is the measured optical rotation; $E_r$ and $E_m$ are the electric fields of the linearly polarized reference (c) and measurement (b') beams, respectively; $\Delta\omega = \omega_r - \omega_m$ is the angular frequency of the heterodyne signal, a is the amplitude of the background heterodyne signal, representing the amount of polarization noise along the optical path and DC is the direct current component.

When the optical rotation angle θ is very small, equation (1) can be simplified:

$$I_m \propto 2\theta \cdot E_r E_m \cos(\Delta\omega t) + aE_r E_m \cos(\Delta\omega t) + DC \quad (2)$$

The horizontal component (f), reaching the reference detector 10, generates a reference photocurrent ($I_r$) proportional only to the laser radiation and the amount of polarization noise along the optical path:

$$I_r \propto aE_r E_m \cos(\Delta\omega t) + DC \quad (3)$$

The reference photocurrent ($I_r$) can be used to subtract the contribution of the various sources of polarization noise from the optical activity signal.

The reference and measurement signals from the reference 10 and measurement 11 detectors are stored and compared by an electronic circuit 12, which produces a comparison signal indicating the amount of optical rotation imparted by the optically active substance in the solution, and, therefore, its concentration. This comparison signal is given by equation (4):

$$I_m - I_r \propto E_r E_m \cos(\Delta\omega t) 2\theta \quad (4)$$

As is evident from equation (4), this Fizeau-based polarimeter is capable of distinguishing between the polarization angle-dependent heterodyne signal and the background heterodyne signal, which is always present. This feature can become very important when a reference (blank) sample cannot be measured in order to enable background subtraction.

Figure 2A:
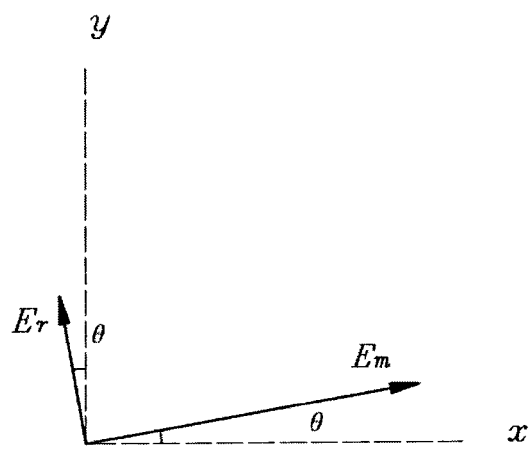
FIGS. 2a and 2b are vector diagrams showing the direction of the electric field vectors of the linearly polarized reference ($E_r$) and measurement ($E_m$) beams in the embodiments of the invention, after they are formed by the partially reflecting mirror (2a) and their second pass through the solution of the optically active substance (2b).
Figure 2B:
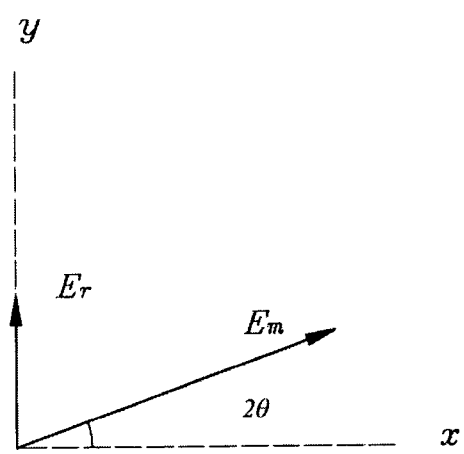

FIGS. 2a and 2b show the direction of the electric field vectors of the linearly polarized reference ($E_r$) and measurement ($E_m$) beams in the embodiments of the invention, formed by the partially reflecting mirror, before the second pass through the solution of the optically active substance—the measurement beam being after passing twice the quarter λ wave plate—(2a) and after their second pass through the solution of the optically active substance (2b).

When there is no optically active substance in the measurement cell, and the optical components of the polarimeter behave ideally, the linearly polarized measurement and reference beams remain perfectly orthogonal and no heterodyne signal will be generated and detected. On the other hand, an optically active substance in the measurement cell will first rotate the electric field vector of the first linearly polarized beam. Consequently, the electric field vectors of the resulting reference and measurement beams will be rotated by a certain angle θ, as shown in FIG. 2a. On their way back through the measurement cell, the electric field vectors, of both the reference and measurement beams, are again rotated by the optically active substance, but this time, as shown in FIG. 2b, the electric field vector of the reference beam ($E_r$) will return to its original position, while the optical rotation of the electric field vector of the measurement beam ($E_m$) will be doubled. When the reference and measurement beams interfere in the presence of an optically active substance, an optical activity-dependent heterodyne signal will be generated at the measurement detector. No such optical activity-dependent heterodyne signal should be detected by the reference detector, since, as also shown in FIG. 2b, the electric field vector of the reference beam ($E_r$) has no component in the direction of the horizontal (x) axis.

Figure 3:
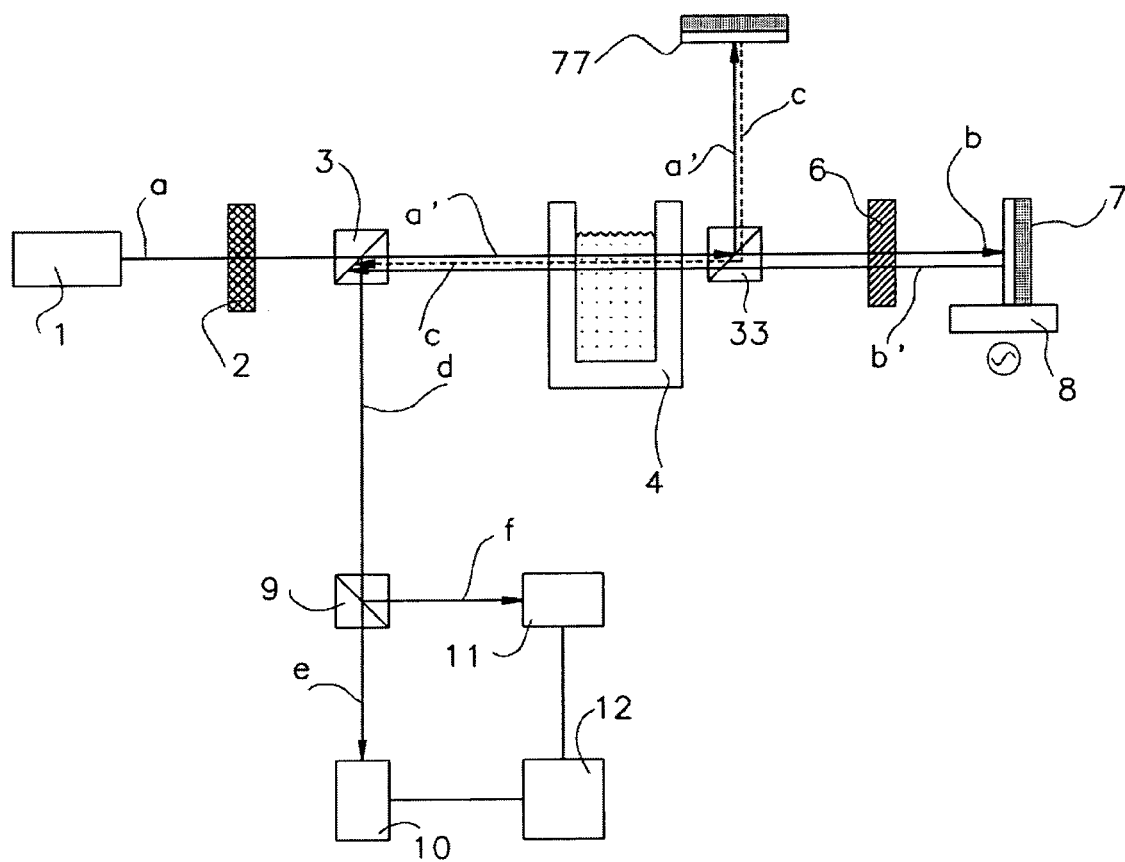
FIG. 3 is a block diagram of a polarimeter according to a second embodiment of the invention where light paths a, a', b, b', c and d of the Fizeau interferometer are formed, but light paths a' and c are only partially shared with the main axis defined by a, b and b', since the partially reflecting mirror of the interferometer is replaced by an asymmetric beam splitter and a fully reflecting mirror, positioned outside its main axis and perpendicular to it, in order to reduce the effect of multiple reflections. Light paths e and f are formed in the detection setup. In the figure: 1. laser source; 2. polarizer; 3. 50:50 beam splitter/combiner; 4. measurement cell containing a solution of an optically active substance; 33. asymmetric beam splitter; 6. quarter λ wave-plate (with its fast axis set at 45 degrees with respect to the polarimeter's main plane); 7. fully reflecting mirror mounted on a PZT-actuated translation stage; 8. PZT-actuated translation stage; 77. fully reflecting mirror; 9. polarizing beam splitter; 10. reference detector; 11. measurement detector; 12. signal processing electronics.

FIG. 3 shows a scheme of a device for the quantitative determination of optically active substances in a solution, conforming to a second exemplary embodiment. The device includes a laser source that emits coherent light. The wavelength of the emitted light can typically range from 400 nanometers to 900 nanometers.

The laser source 1 generates a first coherent light beam (a). The first light beam (a) passes through a polarizer 2, with a transmission axis parallel to the polarimeter's main plane, and becomes linearly polarized. The first linearly polarized beam (a) passes through a 50:50 beam splitter/combiner 3 and is split into linearly polarized reflected and transmitted beams.

The transmitted first linearly polarized beam (a') traverses the measurement cell 4, holding a solution of an optically active substance, whose concentration is to be determined, and its electric field vector is rotated by a certain amount by the optically active substance. When this linearly polarized beam (a') exits the measurement cell, it is split, asymmetrically, by an asymmetric beam splitter 33 into a measurement (b) and reference (c) linearly polarized beams.

The linearly polarized reference beam (c), which typically acquires only 5-10% of the light intensity, is directed to a fully reflecting mirror 77 placed outside the main optical axis of the interferometer and perpendicular to it. It is then reflected exactly in the reverse direction and passes again through the measurement cell 4.

The replacement of the partially reflecting mirror (5 of FIG. 1), by the asymmetric beam splitter 33 and the fully reflecting mirror 77, is designed to reduce interference by multiple reflections between this partially reflecting mirror and the fully reflecting mirror 7, mounted on the PZT-actuated translation stage 8, as in the first embodiment. Such multiple reflections can add heterodyne signals at even multiples of the desired frequency. The laser power loss, caused by the additional beam splitter 33, can be minimized by choosing an asymmetric splitting ratio, typically around 20:80, making the power ratio between the reference and measurement beams approximately 1:10. Another advantage of this setup is that laser sources with short coherence lengths can now be used, since the paths of the reference and measurement beams can be adjusted to become nominally equal.

The following steps in this second embodiment are exactly the same as in the first embodiment above.

When the linearly polarized reference beam (c) traverses the measurement cell 4 in the reverse direction, its electric field vector is rotated by the optically active substance in the solution. However, this time the optical rotation cancels entirely the optical rotation accumulated during the passage of the first linearly polarized beam (a') in the forward direction and, therefore, the linearly polarized reference beam acquires no net optical rotation.

The linearly polarized measurement beam (b), which is transmitted by the asymmetric beam splitter 33 in the original direction, passes a through a quarter λ wave-plate 6, with a fast axis set at 45 degrees with respect to the polarimeter's main plane, and becomes temporarily circularly polarized. The circularly polarized measurement beam (b) is reflected in the reverse direction by a fully reflecting mirror 7, mounted on a piezo-actuated translation stage 8 having a long traveling range.

The piezo-actuated translation stage 8 is driven by a low frequency ramp or triangle waveform, moving the mirror several hundred micrometers in each cycle and shifting the optical frequency of the circularly polarized measurement beam (b) by the "Doppler effect". This frequency shift is typically in the range of several hundred Hertz to several kilohertz. The frequency-shifted and reflected circularly polarized measurement beam (b') passes again through the quarter λ wave-plate 6 and returns to be linearly polarized, with its electric field vector now mirrored about the fast axis of the quarter λ wave-plate 6. When no optical activity is present in the solution, this mirroring by the quarter λ wave-plate 6 rotates the electric field vector of the linearly polarized measurement beam (b') by exactly 90 degrees with respect to the polarimeter's main plane. When an optically active substance is present in the solution, the deviation from 90 degrees is proportional to its concentration.

The linearly polarized frequency-shifted measurement beam (b') returns through the measurement cell and its electric field vector again is rotated by the optically active substance, so that its total optical rotation angle is doubled.

When both the linearly polarized reference (c) and measurement (b') beams reach the beam splitter/combiner 3 on their way back, they are combined and interfere with each other and 50 percents of the combined beam are directed to a polarizing beam splitter 9. The polarizing beam splitter 9 splits the combined beam into its two orthogonal components (e) and (f) and sends the horizontal component (f) to the reference detector 10 and the vertical components (e) to the measurement detector 11.

The horizontal component (f), reaching the reference detector 10, generates a reference photocurrent ($I_r$) proportional only to the laser radiation and the amount of polarization noise along the optical path.

The vertical component (e) reaching the signal detector 11 generates a coherently detected measurement signal of the heterodyne type, with a frequency which is determined by the velocity of the fully reflecting mirror 7. The amplitude of the coherently detected measurement signal represents the concentration of the optically active substance in the solution held in the measurement cell 4, as well as the amount of polarization noise along the optical path.

The reference and measurement signals from the reference 10 and measurement 11 detectors are stored and compared by an electronic circuit 12, which produces a comparison signal indicating the amount of optical rotation imparted by the optically active substance in the solution, and, therefore, its concentration.

The invention claimed is:

1. A method for measuring the optical rotation of a polarized light beam by an optically active substance, using a polarimeter based on a modified Fizeau interferometer, comprising the steps of:
    a) generating by a laser a first coherent light beam of a first frequency;
    b) linearly polarizing said first light beam by passing it through a polarizer so that its electric field vector becomes parallel to the main plane of the polarimeter, defined by the polarizer's transmission axis and the beam's direction;
    c) directing said first linearly polarized light beam through a modified Fizeau interferometer, whereby:
        (i) said first linearly polarized light beam of a) is split, so that one part of it is reflected at an angle with respect to the original direction, and the other part is transmitted in the original direction;
        (ii) said transmitted first linearly polarized light beam is passed through a sample comprising an optically active substance and its electric field vector is rotated by said optically active substance;
        (iii) said transmitted first linearly polarized light beam is then partially reflected and partially transmitted, so that second and third linearly polarized light beams are generated, and said second linearly polarized light beam, which is reflected, is a reference beam, and said third linearly polarized light beam, which is transmitted, is a measurement beam;
        (iv) said linearly polarized reference beam returns along the path of said first light beam through the sample and its electric field vector is rotated by said optically active substance in the sample, so that said linearly polarized reference beam accumulates no net optical rotation with respect to said first linearly polarized light beam;
        (v) the electric field vector of said measurement beam is rotated by mirroring it around an axis set at 45 degrees with respect to the polarimeter's main plane;
        (vi) the optical frequency of said measurement beam, with rotated electric field vector, is shifted by an amount ranging from several hundred Hertz to several kilohertz, so that said measurement beam, with rotated electric field vector, now has a second frequency different from said first frequency;
(vii) said measurement beam, with rotated electric field vector and second frequency, is completely reflected, so that it returns along its original path through said sample of optically active substance;
(viii) the electric field vector of said linearly polarized measurement beam is rotated on its way back through said sample by said optically active substance, so that the optical rotation of said linearly polarized light beam, imparted by said optically active substance, is doubled with respect to said first linearly polarized light beam;
(ix) said linearly polarized reference and measurement light beams transmitted by said sample are combined and interfere to generate a fourth light beam;
d) splitting said fourth light beam into fifth and sixth linearly polarized orthogonal light beams;
e) directing said fifth linearly polarized light beam, whose electric field vector is perpendicular to the polarimeter's main plane, to a reference photodetector and generating a reference signal;
f) directing said sixth linearly polarized light beam, whose electric field vector is parallel to the polarimeter's main plane, to a measurement photodetector and generating a coherently detected measurement signal; and
g) storing and processing said reference and measurement signals and generating comparison signals using said reference and measurement signals, said comparison signals indicating the polarization rotation angle imparted to said linearly polarized measurement light beam by said optically active substance.

2. The method of claim 1, wherein said optically active substance of (ii) is in a solution held in a measurement cell and said measurement cell has transparent walls.

3. The method of claim 1, wherein said comparison signals of (g) are used to quantitatively measure the concentration of said optically active substance in said solution.

4. The method of claim 1, wherein most of the light intensity of said transmitted first linearly polarized light beam in c) (iii) is transferred to said linearly polarized measurement beam.

5. The method of claim 1, wherein in (v) the optical frequency of said linearly polarized measurement beam, with rotated electric field vector, is not shifted, but its phase is periodically modulated by a sine waveform at a frequency which is preferably several kilohertz, and amplitude which is preferably smaller than $\pi/2$ radians.

6. A polarimeter for measuring the optical rotation of a linearly polarized light beam by an optically active substance, comprising:
a) a laser source for generating a first coherent light beam of a first frequency;
a) a polarizer for linearly polarizing said first light beam, whose transmission axis, together with the beam's direction, defines the main plane of the polarimeter;
b) a modified Fizeau interferometer comprising:
(i) a beam splitter for splitting said first linearly polarized light beam, so that one part of it is reflected at an angle with respect to the original direction, and the other part is transmitted in the original direction;
(ii) means for holding a sample comprising an optically active substance on the path of said transmitted part of said first linearly polarized light beam;
(iii) a partially reflecting mirror placed after the means for holding a sample comprising an optically active substance for generating second and third linearly polarized light beams from said transmitted first linearly polarized light beam, said second linearly polarized light beam, which is reflected exactly in the reverse direction, is a reference beam, and said third linearly polarized light beam, which is transmitted in the original direction, is a measurement beam;
(iv) a quarter $\lambda$ wave-plate, whose fast axis is set at 45 degrees with respect to the polarimeter's main plane, for rotating the electric field vector of said linearly polarized measurement beam;
(v) a frequency shifter, for shifting the optical frequency of said measurement beam, with said rotated electric field vector, so that said linearly polarized measurement beam will have a second frequency different from said first frequency;
(vi) a fully reflecting mirror for reflecting said measurement beam, with said rotated electric field vector and said second frequency, exactly in the reverse direction, whereby said reflected measurement beam returns along its original path through said quarter $\lambda$ wave-plate, so that its electric field vector is rotated by mirroring it around an axis set at 45 degrees with respect to the polarimeter's main plane, and said measurement beam transmitted by said quarter $\lambda$ wave-plate then passes through said sample, so that its electric field vector is rotated by said optically active substance, thereby doubling the optical rotation of the transmitted first linearly polarized light beam imparted by said optically active substance;
(vii) a beam combiner for combining and interfering said linearly polarized reference beam and measurement beam transmitted through said sample and generating a fourth light beam, wherein said beam combiner and said beam splitter of (i) are essentially the same optical element;
c) a polarizing beam splitter for splitting said fourth light beam into fifth and sixth linearly polarized orthogonal light beams;
d) a reference photodetector for receiving said fifth linearly polarized light beam and generating a reference signal;
e) a measurement photodetector for receiving said sixth linearly polarized light beam and generating a coherently detected measurement signal, proportional to the polarization rotation angle imparted to said linearly polarized measurement beam by said optically active substance; and
f) electronic means for storing and processing said reference and measurement signals and for generating comparison signals using said reference and measurement signals, said comparison signals indicating the polarization rotation angle imparted to said linearly polarized measurement beam.

7. The polarimeter of claim 6, wherein said means of c) (ii) for holding said sample comprising the optically active substance is a measurement cell with transparent walls and said optically active substance is in a solution.

8. The polarimeter of claim 6, wherein said comparison signals of (g) are used for quantitatively measuring the concentration of said optically active substance in said solution.

9. The polarimeter of claim 6, wherein said partially reflecting mirror of (iii) transmits most of the light intensity of said first linearly polarized light beam.

10. The polarimeter of claim 9, wherein said partially reflecting mirror is placed outside the main optical axis of said modified Fizeau interferometer, perpendicularly to said main optical axis, and a second beam splitter is placed between said means of (c, ii) for holding a sample of said optically active substance and said quarter λ wave-plate of (c, iv), wherein said second beam splitter is for splitting said first linearly polarized beam into measurement and reference linearly polarized beams, and said partially reflecting mirror is for reflecting said reference linearly polarized beam back to the second beam splitter.

11. The polarimeter of claim 10, wherein said partially reflecting mirror is replaced by a fully reflecting mirror and said second beam splitter is an asymmetric beam splitter.

12. The polarimeter of claim 6, wherein said frequency shifter is said fully reflecting mirror of (c, vi) mounted on a piezoelectric (PZT) transducer-actuated translation stage, driven by a ramp or triangle waveforms.

13. The polarimeter of claim 6, wherein said frequency shifter is replaced by a phase modulator for periodically modulating the phase of said linearly polarized measurement beam at a frequency of several kilohertz, with a sine waveform and amplitude, which is preferably less than $\pi/2$ radians, so that the phase of said linearly polarized measurement beam will periodically change with respect to the phase of said linearly polarized reference beam.

14. The polarimeter of claim 13, wherein said phase modulator is said fully reflecting mirror mounted on a PZT-actuated translation stage.

15. The polarimeter of claim 13, wherein said phase modulator is a thin PZT disk coated by a reflecting layer.

16. The polarimeter of claim 6, wherein said laser light source, polarizer, beam splitters, frequency shifter or phase modulator, quarter wave-plate, minors and photodetectors are independent components, such as cube beam splitters, calcite polarizers and coated glass lenses.

17. The polarimeter of claim 6, wherein some or all of said light source, polarizer, beam splitter, frequency shifter or phase modulator, beam combiner, quarter λ wave-plate, mirrors and photodetectors are integrated optical components, based on a waveguiding platform.

* * * * *